(12) United States Patent
Howard

(10) Patent No.: US 9,956,080 B1
(45) Date of Patent: May 1, 2018

(54) REDUCED-FRICTION JOINT WITH ELECTROMAGNETICALLY SEPARABLE BEARING SURFACES

(71) Applicant: Jason Howard, Halifax (CA)

(72) Inventor: Jason Howard, Halifax (CA)

(73) Assignee: Jason Howard, Doha (QA)

( * ) Notice: Subject to any disclaimer, the term of this patent is extended or adjusted under 35 U.S.C. 154(b) by 0 days. days.

(21) Appl. No.: 14/175,541

(22) Filed: Feb. 7, 2014

Related U.S. Application Data

(60) Provisional application No. 61/762,516, filed on Feb. 8, 2013.

(51) Int. Cl.
| | |
|---|---|
| *A61F 2/30* | (2006.01) |
| *A61F 2/32* | (2006.01) |
| *A61F 2/38* | (2006.01) |
| A61F 2/42 | (2006.01) |

(52) U.S. Cl.
CPC .................. *A61F 2/32* (2013.01); *A61F 2/38* (2013.01); *A61F 2/4202* (2013.01); *A61F 2002/30054* (2013.01); *A61F 2002/30079* (2013.01); *A61F 2002/30598* (2013.01); *A61F 2002/30649* (2013.01)

(58) Field of Classification Search
CPC .. A61F 2002/30054; A61F 2002/30079; A61F 2002/301; A61F 2002/30668; A61F 2002/4698

USPC ....................................................... 623/18.12
See application file for complete search history.

(56) References Cited

U.S. PATENT DOCUMENTS

| | | | | |
|---|---|---|---|---|
| 3,798,679 | A | * | 3/1974 | Ewald .......................... 623/20.31 |
| 4,024,588 | A | | 5/1977 | Janssen et al. |
| 4,835,506 | A | | 5/1989 | Leupold |
| 5,755,803 | A | * | 5/1998 | Haines et al. .............. 623/20.14 |
| 6,633,217 | B2 | | 10/2003 | Post |
| 6,758,146 | B2 | | 7/2004 | Post |
| 7,101,374 | B2 | | 9/2006 | Hyde, Jr. |
| 8,273,130 | B2 | | 9/2012 | Gradl |
| 2002/0032484 | A1 | * | 3/2002 | Hyde, Jr. ................... 623/18.12 |
| 2003/0005849 | A1 | * | 1/2003 | Post ................................ 104/2 |
| 2010/0036493 | A1 | | 2/2010 | Simon |
| 2010/0331993 | A1 | * | 12/2010 | Gradl ........................... 623/23.4 |

* cited by examiner

*Primary Examiner* — Marcia Watkins

(57) ABSTRACT

The disclosure provides a joint replacement coupling comprising joint members with opposing joint surfaces, wherein one of the members has a magnetic portion therein which comprises an array of magnets, and the other of the members has a conduction portion therein that comprises a conductive surface. The magnets are arranged to produce a magnetic field that contacts the conduction portion. The conduction portion is optionally positioned so that at least a portion of the conductive surface contacts the magnetic field so that relative motion between the opposing joint surfaces induces current loops in the conductive surface and produces a repulsive force against the magnetic portion, thereby reducing friction between the joint surfaces, optionally separating the joint surfaces.

20 Claims, 6 Drawing Sheets

REDUCED-FRICTION JOINT WITH ELECTROMAGNETICALLY SEPARABLE BEARING SURFACES

CROSS-REFERENCE TO RELATED APPLICATIONS

This application claims priority to US provisional application no. 61/762,516, filed Feb. 8, 2013, which is incorporated by reference herein in its entirety.

TECHNICAL FIELD

This invention is related to the field of wear reduction, and reducing the production of wear particles, in total joint replacement by the use of magnetic repulsion between opposing bearing surfaces.

BACKGROUND

Current total joint replacement ("TJR") designs—though tremendously successful in patients with limited activity levels and lifespan—are not optimal for the increasing population of more active and younger patients with advanced degenerative joint disease. These patients have a higher likelihood of implant failures secondary to an inflammatory response initiated by wear particle debris. A new approach in TJR design which minimizes the generation of wear particles through the reduction of frictional forces within the joint is required to address the unique and demanding needs of this patient population.

SUMMARY OF THE DISCLOSURE

The disclosure relates to a magnetic bearing couple utilizing the principles of electromagnetic induction to reduce wear particle production in TJR. The TJR device promotes fluid-film lubrication (i.e. reducing friction between bearing surfaces and optionally providing partial or complete separation of the two bearing surfaces during joint motion).

In particular, this application discloses a TJR device using electromagnetic induction to produce a stable repulsive magnetic force that promotes the separation of opposing joint surfaces (such as for the hip, knee, and ankle).

The disclosure provides a joint replacement coupling optionally comprising joint members with opposing joint surfaces, wherein one of the members has a magnetic portion therein which comprises an array of magnets, and the other of the members has a conduction portion therein that comprises a conductive surface. The magnets are typically arranged to produce a magnetic field that contacts the conduction portion. The conduction portion is optionally positioned so that at least a portion of the conductive surface contacts the magnetic field so that relative motion between the opposing joint surfaces induces current loops in the conductive surface and produces a repulsive force against the magnetic portion, thereby reducing friction between the joint surfaces, optionally separating the joint surfaces (and separating the joint members).

Another embodiment of the invention is a joint replacement coupling optionally comprising:
 a socket and a head;
 wherein one of the socket and the head has a magnetic portion therein which comprises an array of magnets, and the other has a conduction portion therein that comprises a conductive surface,
 the magnets arranged to produce a magnetic field that contacts the conduction portion,
 the conduction portion positioned so that at least a portion of the conductive surface contacts the magnetic field so that relative motion between the head and socket induces current loops in the conductive surface and produces a repulsive force against the magnetic portion, thereby reducing friction between the head and socket, optionally separating the opposing surfaces of the head and socket.

Optionally the socket comprises a liner in which the array of magnets is embedded, the socket configured for connection to a shell or a bone. The head optionally comprises a ball or a plurality of condyles containing the array of magnets, the head configured for connection to a shell or a bone. The array of magnets optionally comprises a plurality of adjacent permanent magnets arranged in a Halbach array, such as a hemi-spherical Halbach array. For example, the array of magnets optionally comprises a hemi-spherical Halbach array implanted within the socket, wherein the femoral head comprises a conductive surface. The Halbach array optionally further comprises i) interstitial permanent magnets inserted in the Halbach array or ii) permanent magnets shaped to focus magnetic flux in an alternating pole pattern. In another embodiment, both the socket and head comprise a hemi-spherical Halbach array. Optionally, the head comprises a bifurcated head with two condyles (dual bearings). The magnetic field source typically produces a changing magnetic field, optionally a sinusoidal magnetic field, directed outwardly from the concave surface, optionally wherein the magnetic field is concentrated at a joint articulation. The magnets are optionally rare earth permanent magnets. The socket or the head optionally comprises a conductive material. The conductive surface optionally comprises copper, aluminum, or electrically-optimized nanocomposite materials, optionally composites of polymers, ceramics, material which incorporates carbon nanotubes or graphene, optionally wherein the conductive surface is coated with a biocompatible coating, optionally titanium nitride. The conductive surface optionally comprises spherically-shaped layers of conductor that are slotted and terminated at sheet ends to direct currents, optionally comprising layers of insulating material located alternatingly between layers of conductor. Optionally most or all of the head surface is the conductive surface. The number of current loops is readily increased to increase the strength of the magnetic field. Optionally the head comprises a conductive material layer covering a spherical core. The femoral head optionally comprises alternating layers of i) conductive material layer, and ii) insulating layer, the layers spherically shaped and covering a spherical core. The head optionally comprises thermally conductive metal, optionally wherein the metal comprises heat sinks. The socket optionally fits in a shell, optionally an acetebular shell, or is directly connectable to bone, and ii) the head is connectable to a femoral stem.

The joint replacement is total hip replacement and i) the head comprises a femoral head having a femoral head bearing surface, the femoral head configured to be connected to a femoral stem to be fixed in the subject's bone; and ii) the socket comprises an acetebular socket having a bearing surface that is configured with a round concave portion to receive the femoral head bearing surface, the socket configured to be connected to a shell or bone.

Optionally the bearing surfaces are coated, optionally coated with titanium nitride, high density polyethylene, a cobalt alloy, or a magnetically permeable nano-composite material. Optionally a first Halbach array is embedded in the socket, a second Halbach array is embedded in the femoral head, and a conducting material portion (optionally, a laminated stack of slotted conducting sheets as discussed previously) that is spherical in shape articulates between the first and second Halbach arrays.

The disclosure also includes use of the devices described herein for total joint replacement. A method of providing a total joint replacement in a subject in need thereof, is also provided optionally comprising implanting a device herein in the subject.

In an example of a THR embodiment, the joint replacement coupling comprises: a socket and a head (typically a ball), wherein the socket comprises an array of magnets therein, and the head comprises a conductive surface. They are optionally arranged to produce a magnetic field that contacts the head. The head is typically positioned so that at least a portion of the conductive surface contacts the magnetic field so that relative motion between the head and socket induces electric current loops in the conductive surface and produces a repulsive force against the socket, thereby separating the head and socket and reducing friction between the head and socket. The relative motion is typically along a path that is optionally an arc-shaped path or flat path between the socket and head (ie. between the bearing surfaces ie articulating surfaces).

In another embodiment, the disclosure provides a joint replacement in the coupling for a joint, such as a hip joint. Optionally the system comprises a socket case including a housing, optionally a curved housing, having first and second ends, the housing having a joint facing surface that is optionally convex and fits within the joint socket, and a head socket facing surface that is optionally concave and forming a base socket surface, optionally an arc shaped surface, between the first and second ends of the housing. A plurality of adjacent magnets are received in the housing and optionally aligned in a magnet arc along the head socket arc (in other couplings, the magnets may be arranged in a generally linear array), the magnets arranged in a Halbach array, the array forming a magnetically enhanced surface, optionally a curved surface, aligned with the head facing surface and a demagnetized surface aligned with the socket facing surface, the array producing a magnetic force (optionally a sinusoidal force) directed outwardly from the concave surface. The device also optionally includes a head that fits in the head socket facing, the head having an electrically conductive surface, wherein movement of the socket case and head relative to each other contacts the magnetic force with the electrically conductive surface and generates current loops in the electrically conductive surface to produce a force outwardly from the head in a direction that opposes the magnetic force.

In another embodiment, the joint replacement coupling comprises a total knee replacement coupling and i) the socket comprises a tibial component with two condyles, each condyle optionally with a permanent array of magnets therein, typically a linear array, and ii) a head comprising two condyles with a conducting portion comprising a conductive surface. Optionally a conducting material and conductive surface is embedded within the opposing trochlear (central) groove region of the femoral component. Optionally only a portion of a coupling described in this application is provided, for example for the knee, optionally only a coupling for replacing the knee joint compartment (patellofemoral element) is provided. Similarly, for the hip, the head or the socket is optionally the only component provided.

In another embodiment, an array of magnets is in the condyles of the femoral component and the top surface of the tibial tray component. A conducting portion is optionally embedded in the tibial liner and articulates as an intercalated segment between these two arrays to induce current loops in the surfaces above and below the segment, thereby producing force to oppose the magnetic fields. The intercalated tibial liner optionally permits rotation at the tray-liner articulation and the flexion-extension knee range of motion occurs at the condyle-liner articulations.

In another embodiment, the total joint replacement is a total ankle replacement, wherein in the coupling a magnet portion comprises an array of magnets (optionally a linear or curved array) that is in a distal tibial component liner. The liner is optionally configured to connect to the locking mechanism in a tibial replacement component or configured for connection to the subject's distal tibial bone. Optionally the talar component comprises a conducting portion comprising a conducting surface in which induced currents form. An alternative embodiment includes an intercalated segment and dual arrays of magnets. The arrays are optionally in a distal tibial liner and in the talar component, both of which are affixed to bone. A conducting portion having conductive surfaces is embedded between these two arrays with currents induced at the conductive surfaces. The implant is constrained to permit rotation at the superior articulation while flexion-extension ankle range of motion occurs at the inferior articulation. Induced currents and stable repulsive magnetic fields generated at these articulations reduce friction of the bearing surfaces involved.

Other embodiments and advantages will be readily apparent.

BRIEF DESCRIPTION OF THE DRAWINGS

Certain embodiments of the invention will be described below in relation to the drawings.

DETAILED DESCRIPTION

Figure 1:
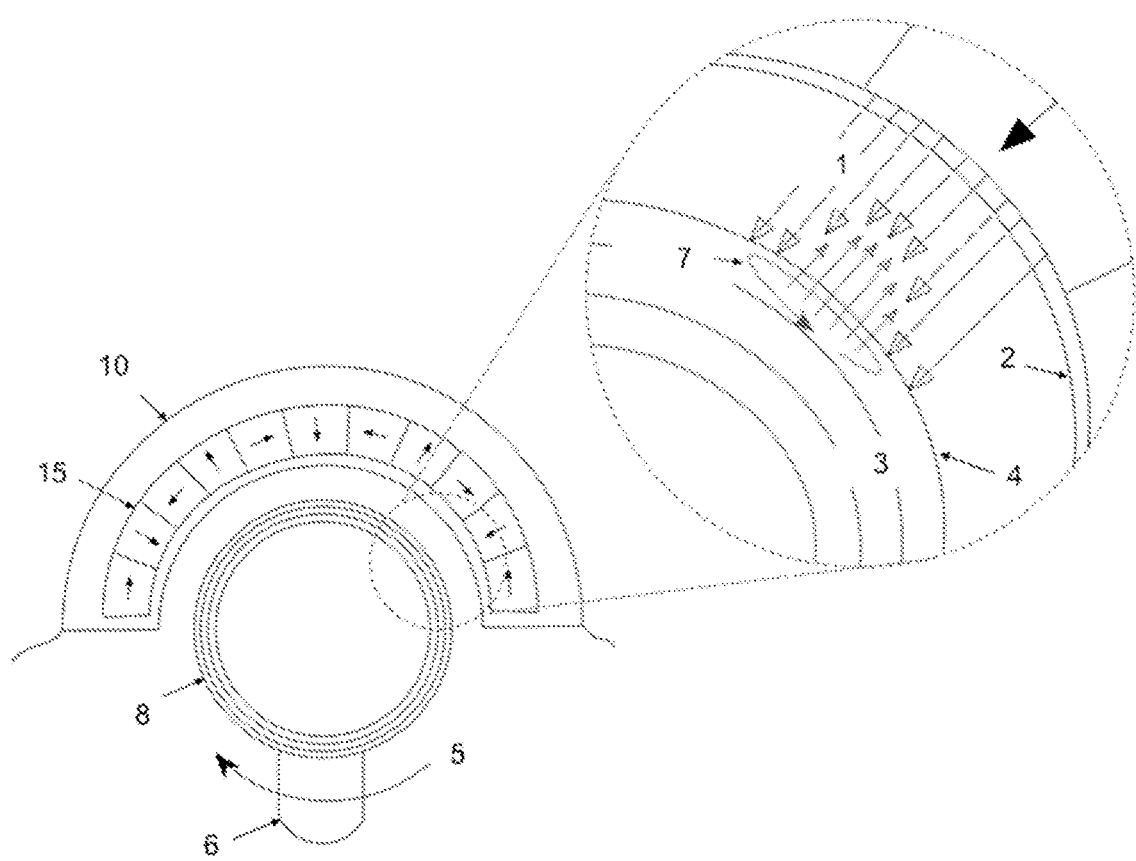
FIG. 1 provides a diagrammatic view of the proposed passive electromagnetic suspension system for wear reduction in a total hip replacement bearing couple. A hemispherical Halbach array implanted within the acetabular liner induces electric currents in a suitably conductive moving femoral head component

The application describes a device that incorporates passive electromagnetic induction to reduce friction and, optionally, separate TJR bearing surfaces through the development of a stable, repulsive magnetic force.

In one embodiment, the disclosure provides a joint replacement coupling comprising opposing joint surfaces, wherein one of the surfaces has an array of magnets therein, and the other of the surfaces has a conductive surface. The magnets are typically in a magnetic portion located in or below the surface of a member of the coupling. The conductive surface is typically located in or on in a conduction portion of a member of the coupling. The magnets are arranged to produce a magnetic field that contacts the conductive surface, wherein relative motion between the opposing joint surfaces induces current loops in the conductive surface and produces a repulsive force against the magnetic field. This force reduces friction between the joint surfaces, optionally separating the joint surfaces. The joint replacement coupling is optionally for hip, shoulder, knee or ankle total joint replacement in a subject in need thereof.

The resultant force may reduce friction between the surfaces while they remain in contact, or there may be partial or complete separation of the opposing joint surfaces (also called articulation surfaces). Optionally, there are two opposing joint surfaces (eg. hip) or more depending on the joint involved (eg. the knee joint has 3 separate articulations: patellofemoral, medial femoro-tibial, lateral femoro-tibial). Separation refers to the presence of space between the bearing surfaces, allowing for fluid film lubrication in the joint.

In another embodiment, the disclosure provides a joint replacement coupling with a socket and a head. In certain embodiments, the head is a ball, which is typical for hip replacement. In other embodiments, the head is a bifurcated head that contains more than one condyle (sub-head), each with its own articulation surface, as for the femoral component in total knee replacement (TKR). Likewise, the socket can also be bifurcated into two articulating surfaces, as for the tibial component in TKR. In the ankle, the head is represented by the talar joint surface and the socket is represented by the distal tibial joint surface. In total shoulder replacement, the head is a ball and is represented by the proximal humeral joint surface while the socket is represented by the glenoid joint surface. Optionally, one of the socket and head has a magnetic portion therein which comprises an array of magnets, and the other has a conduction portion therein that comprises a conductive surface. Each condyle of a bifurcated head would contain a condyle magnetic segment, the segments together making up the magnetic portion of the head. Optionally, each condyle of a bifurcated head would contain a conducting portion, the segments together making up the conducting portion of the head. The magnets are typically arranged to produce a magnetic field that contacts the conduction portion. The conduction portion is readily positioned so that at least a portion of the conductive surface contacts the magnetic field so that relative motion between the head and socket induces current loops in the conductive surface. This produces a repulsive force against the magnetic portion, thereby separating the opposing surfaces of the head and socket and reducing friction between the head and socket. The socket is configured to be attached directly to bone or to be attached to a shell that is in turn attached directly to bone. The head is configured to be attached to a stem that is in turn fixed directly to bone.

With reference to FIG. 1, the repulsive force is generated from the interaction of a changing (time-varying, geometrically-varying, or both) magnetic field(s) 1 embedded in one or more TJR components with electrically conductive elements 3 embedded in one or more opposing joint components. When there is relative motion 5 along the path between the bearing surfaces, this interaction results in the induction of electric currents 7 that, in turn, result in the development of a stable opposing magnetic field that reduces joint reaction force and promotes separation of the bearing surfaces. The path is variable, for example, optionally arc-shaped or flat. Certain embodiments are described in detail below with respect to their application to total hip replacement ("THR") devices. This disclosure is not limited to the hip joint, nor to humans only.

Figure 2:
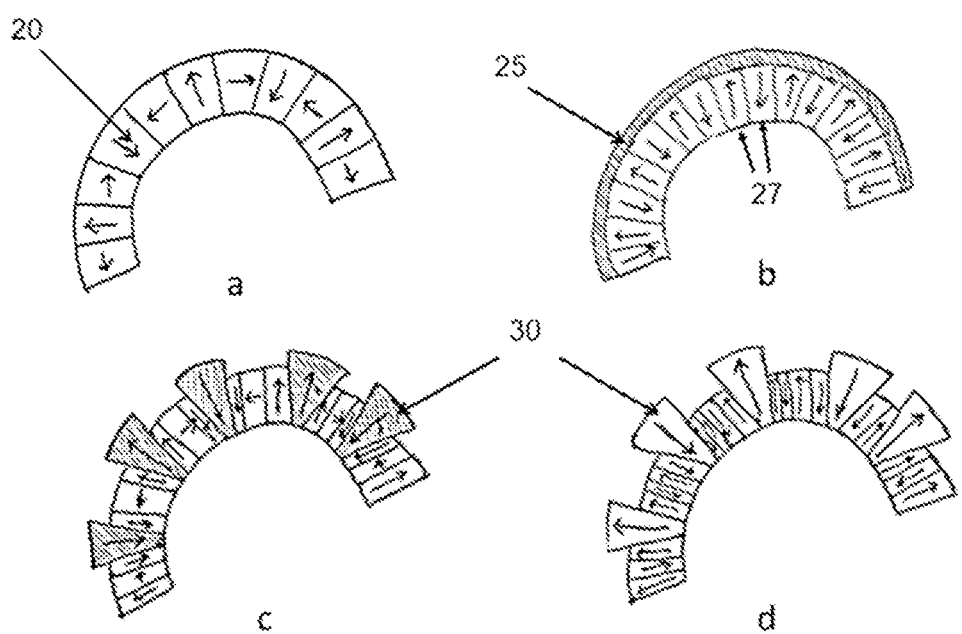
FIG. 2 shows several geometric arrangements of the permanent magnet array within the acetabular component as alternative embodiments for this invention. These include (a) the use of a hemi-spherical Halbach array, (b) alternating poles with magnetic shielding, (c) augmentative fields from focused magnetic flux via cone or funnel shaped interstitial magnets within a Halbach arrangement, or (4) augmentative fields from focused magnetic flux via cone or funnel shaped interstitial magnets within an alternating pole arrangement. Arrows within constituent magnets indicates the direction of polarity for each.

In the first embodiment referring to THR, the femoral head 8 has a spherical core 42 which is configured to be connected to a commercially available femoral stem component 6. The femoral stem 6 is to be fixed in the subject's bone. The femoral head 8 also has a femoral head bearing surface 4. Examples of suitable femoral stems include both cemented and uncemented varieties which are implanted within the medullary cavity of the proximal femur. The socket bearing surface 2 (also called acetabular bearing surface for hip) is configured with a round concave portion to receive the femoral head bearing surface 4. The socket liner 10 is configured to be either connected to a commercially available socket shell (also called acetabular shell for hip) or directly affixed to the subject's bone. In FIG. 1, the hemi-spherical Halbach array 15 implanted within the socket liner 10 induces electric currents 7 in a suitably conductive moving femoral head component 8. For the Halbach array, the magnets are typically arranged such that the field orientation of each magnet is 90 degrees, or less, relative to the next magnet. The resultant magnetic flux generated opposes the initial field 1 reducing friction between the implant surfaces, optionally partially or completely separating the surfaces. Arrows within the constituent magnets 15 show the direction of polarity for each. The generation of sufficient repulsive magnetic force between the bearing surfaces (femoral head 8 and acetabular or socket 10 components) of a THR device is achieved via configuration of the socket-based applied magnetic field source 15 and femoral head-based conducting material configuration 5 (FIG. 1). Although the description detailed herein involves the use of fields sourced from permanent magnets, the use of electromagnets (with or without active control elements) is included in this disclosure. Opposing repulsive fields are realized via currents (and their respective magnetic fields) induced 7 in the conducting material configuration 3 (described below) present in the femoral head component 8. A reversal of placement by putting magnets in the socket and conducting material configuration in the femoral head would also generate stable repulsive fields. The magnetic field source 15 in FIG. 1 is located in the acetabular (socket) liner component 10 and optionally consists of high strength rare earth permanent magnets (optionally, grade N48 or higher NdFeB or equivalent) arranged in such a way as to generate a maximally changing (or periodic) field. Several geometric arrangements of permanent magnets 20 within the socket liner are considered as alternative elements for this invention. These include the use of a hemi-spherical Halbach array (FIG. 2a), alternating poles with magnetic shielding 25 (FIG. 2b), a hybrid Halbach array which incorporates augmentative fields and focused magnetic flux from spaced interstitial permanent magnets 30 (FIG. 2c) or augmentative fields from permanent magnets shaped to focus magnetic flux 30 in an alternating pole pattern (FIG. 2d).

For the hemi-spherical Halbach array element (FIG. 2a), high strength rare earth permanent magnets 20 are optionally arranged as a "cup" with inner and outer diameters determined by the height of the magnet array to increase magnetic field strength at the joint surface. The constituent magnets 20 are arranged such that the field orientation of each bar is 90° (or less as required) to the next. This arrangement is configured to result in a near sinusoidal magnetic field density (BH) of optimal wavelength and increased amplitude with subsequent augmentation of the field on the concave (joint) side of the array and cancellation of field on the convex (body) side. This arrangement acts as an effective magnetic shield to the rest of the body with field concentration at the joint articulation and minimization of stray fields. The augmentation of fields from adjacent permanent magnets bars results in the peak amplitude of BH being larger than the field from each individual bar. According to Faraday's Law, maximization of the induced electro-motive force or voltage (and thus the induced currents which generate the opposing magnetic field) is achieved through increasing both the peak amplitude and frequency of the applied field, BH. In the case of the Halbach arrangement, the frequency is proportional to the angular velocity of the joint, and inversely proportional to the wavelength of the array. Increasing the wavelength by decreasing the surface area of the face of each constituent magnet bar serves to increase the induced opposing magnetic field and thus promotes separation of the joint surfaces. The hemi-spherical Halbach array element as described above and shown in FIG. 2a is a typical suitable embodiment.

For the alternating poles alternative element (FIG. 2b), permanent magnets of opposite polarities 27 are arranged adjacent to each other to create an alternating magnetic field. Magnetic field generation in the conducting material (and thus repulsive force) is increased when the length of each magnet's face is significantly smaller than the magnet's height. In addition, the wavelength of the resulting magnetic field can be further decreased by minimizing the area of each source magnet's face. Another alternative element for the permanent magnet field source incorporates additional high strength permanent magnets 30 interspersed at intervals between sections of Halbach array or alternating poles that may be used to augment BH. These interstitial magnets are recessed from the joint surface with each of their respective fields focused through shaping as an inverted cone or funnel (with each flattened tip at the joint surface). The polarity of these interstitial magnets are chosen to augment the "peaks" of the field generated by the Halbach array or alternating poles arrangement. These configurations serve to increase the number of magnetic flux lines per unit area directed into the conductive material within the femoral head component. The number of intestinal magnet assemblies utilized can be varied according to the strength of magnetic force required. These alternative elements are illustrated in FIGS. 2c and 2d.

The generation of stable opposing magnetic fields of sufficient magnitude depends not only on the characteristics of the source field but also on the configuration of the conducting material. In magneto-mechanic applications, the amplitude of induced magnetic field from a wire coil is proportional to the conductivity of the wire and to the number of turns of wire in the coil. Thus, for the purposes of this invention, the chosen conducting material embedded in the femoral head component exhibits a very high electrical conductivity with copper, aluminum, and electrically-optimized nanocomposite materials (i.e. composites of polymers, ceramics, or other materials which incorporate carbon nanotubes, graphene, or other nano-materials) all suitable candidates for use.

In addition to the conductivity of the material, the configuration of the conductor(s) is a consideration. In its simplest form, a uniform conductor deposited onto the femoral head (sealed by an appropriately chosen biocompatible coating, such as titanium nitride) would allow for induction of currents within the surface. It is desirable to increase the amount of magnetic force generation to get a significant reduction in joint reaction force. To increase the effective number of current "loops" using a configuration amenable to manufacture in a hemi-spherical shape, a curved conducting track that increases lift and decreases eddy current losses is useful in the current invention. An example of a conducting material configuration is in FIG. 3. The number of current loops within the conducting material configuration are effectively increased (thereby maximizing the total opposing magnetic field) by stacking spherically-shaped sheets 35 of conductor that are slotted and terminated at the ends 37 to direct currents via defined loops. These sheets are laminated together with an electrically insulating material 40 that is chosen to increase its mechanical strength and bonding capabilities as well as decrease parasitic eddy current losses. Typically, the material is highly magnetically permeable to circumvent the skin effect that shields the lower conductors from the applied magnetic field and thus allow for a more even distribution of current density throughout the stack via inductive loading. A 3-D view demonstrating the slots and terminations, as well as the female end of the morse taper 44 or equivalent connection to the femoral stem, is shown in FIG. 2a. The stacked conducting sheets (dark lines) 35 laminated together and bonded onto a spherical core 42 with the female end of a morse taper 44 or equivalent are shown in an illustrative cross-section FIG. 2b.

The insertion of thin highly magnetically permeable strips that span the entire depth of the conducting sheets 35 in the femoral head is an alternative to the choice of a highly magnetically permeable material for the electrically insulating material 40 described in the preceding paragraph. For both embodiments, the materials are typically highly magnetically permeable but not ferromagnetic (to avoid attraction between the bearing surfaces).

The method of manufacture for the stacked spherical conducting material configuration as above is included in the disclosure. Therefore, the invention includes a method of manufacture of a conductive joint replacement coupling head or socket, comprising connecting (eg. depositing or affixing) a uniform conductor onto a head or socket, typically as a continuous layer, and optionally coating the conductor in a case suitable for a joint replacement head or socket. The method optionally comprises producing, optionally by etching, milling or photolithography, slots in a conductive material layer, the slots suitable to produce current loops;

bonding the conductive material to an insulating layer that exhibits magnetic permeability, arranging alternating layers of the conductive material layer and insulating layer;

laminating the alternating layers together to form a laminate, optionally under heat and pressure, optionally by hemi-spherical molding; and wherein the depositing step comprises fixing the laminate over the outer surface of a head core to form a head or a socket core to form the socket.

The depositing step optionally comprises: electro-plating alternating layers of a conductive material layer and an insulating layer onto a head core to form a head or a socket core to form a socket, wherein the conductive material layer has slots to produce current loops, and wherein the insulating layer exhibits magnetic permeability.

The disclosure also includes a method of manufacture of a joint replacement magnetic coupling head or socket, comprising providing a plurality of magnets arranged to form a magnetic field, optionally in a Halbach array; and optionally coating the magnets in a case suitable for a joint replacement head or socket. The disclosure also includes a head or socket manufactured according to a method described herein.

Figure 3:
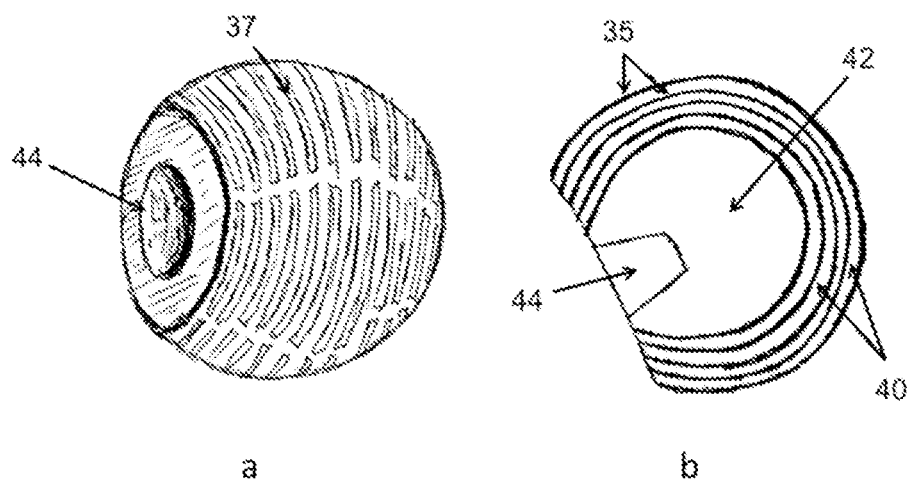
FIG. 3 provides a diagrammatic view of the conducting material configuration as applied to the total hip replacement ("THR") femoral head component.

Sheets of highly conductive material 35 are etched using photolithographic techniques or milled to produce the slots required at the optimal length and width to maximize the number of current loops 37 contributing to the opposing magnetic field. These sheets are bonded to an insulating layer that ideally exhibits high magnetic permeability and mechanical strength in an alternating pattern 40 to a depth constrained by the size of the THR component but configured achieve a maximum number of current loops (FIG. 3). The insulating layers and conducting sheets are laminated together under heat and pressure via hemi-spherical molds or other techniques to bond the surfaces together. An alternative method is to electro-plate the conducting material onto the insulating material substrate that is deposited onto a metal sphere using spray forming techniques, or some variant thereof. Combinations of the processes outlined above will also be considered. The thickness of the conducting sheets and "traces" between the slots will be determined according to anticipated currents with higher values requiring more conducting material to carry them. Heat sinks are incorporated into the spherical core 42 to dissipate heat from generated currents towards the femoral stem component 6 (via the morse taper or equivalent connection 44) or the metal acetabular cup 50 or cement as necessary.

An alternative element involves the use of wire coils embedded in the THR component(s) instead of the stacked conductors as above.

The description of the current invention above involves the use of a single hemi-spherical Halbach array or alternate source magnetic field coupled to a conductor configuration in a single bearing surface interaction. This solution will advantageously result in decreased wear particle generation through the reduction of frictional forces within the joint. It is desirable to generate sufficient magnetic force to achieve complete separation of the joint surfaces. However, even where complete separation is achievable, when the subject first starts to move the joint, there will be a brief period where the ball and socket are in contact during early relative movement. The length of this time period, and the achievement of separation of the surfaces, depends on the relative speed of movement of the joint by the subject. Increasing the magnetic force coupled with the use of highly wettable bearing surface coatings further reduces wear particle generation through fluid-film lubrication. In addition to refining the conducting material configuration and magnetic field source, further distribution of the joint reaction force over a larger surface area is advantageous. Increasing the total surface area of the THR joint(s) by increasing the number of articulating surfaces will be useful in this regard.

To this end, another embodiment that uses a dual bearing design is useful. The disclosure provides a joint replacement coupling comprising opposing joint surfaces, wherein one of the surfaces has a magnetic portion therein which comprises an array of magnets. The magnets are arranged to produce a magnetic field that contacts the conduction portion. The surfaces have a conduction member therebetween that comprises a conductive surface, with the conduction member positioned so that at least a portion of the conductive surface contacts the magnetic field so that relative motion between the opposing surfaces induces current loops in the conductive surface and produces a repulsive force against the magnetic portion. This has the effect of reducing friction between the joint surfaces, optionally separating the joint surfaces. Optionally one of the surfaces is on a head (ie. head surface) and the other is on a socket (ie. socket surface). The conduction member is optionally a conductive sheet configured to fit over the head, for example, when the magnetic portion is in the socket. Alternatively, the conduction member is received in the socket when the magnetic portion is in the head. In another embodiment, both the socket and head have a magnetic portion and, typically, the conduction member is permitted to move relative to the socket surface and head surface and produces a repulsive force against both the magnetic portions.

Figure 4:
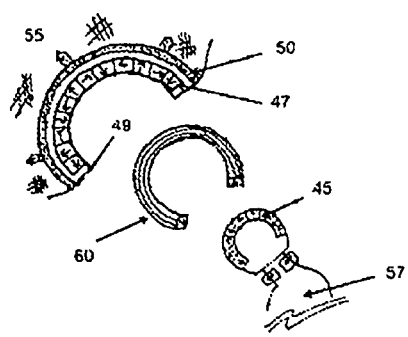
FIG. 4 shows an exploded view of the proposed passive electromagnetic suspension application for wear reduction in total hip replacement utilizing a dual articulation and two magnetic field sources.

FIG. 4 shows hemi-spherical Halbach arrays implanted within both the socket liner 47 and the femoral head 45 to induce electric currents in an intercalated conducting material configuration 60. The conducting material is articulating with the respective joint surfaces. The resultant magnetic flux generated is larger than that generated by a single Halbach array and allows for a greater distribution of force by increasing the effective surface area of the joint. For this embodiment, a magnetic field source (typically a Halbach array or other permanent magnet arrangement as discussed previously) is embedded in the socket liner 49 affixed to the bony pelvis 55 via the socket shell component 50, and a second Halbach array is embedded in the femoral head component attached to a commercially available femoral stem component 57. A conducting material configuration (typically, a laminated stack of slotted conducting sheets as discussed previously) that is spherical in shape but greater than a hemisphere in size will articulate between the two Halbach arrays 60 (FIG. 4). The socket liner 49 magnets and the femoral head 45 magnets provide: (1) an effective doubling of the magnetic field "seen" by the conducting material, (2) a significant increase in the current loops (and subsequent opposing magnetic field generation) induced, and (3) an increased distribution of magnetic force by increasing the effective surface area of the bearing surfaces, as compared to the single permanent magnetic source embodiment.

For both the socket liner 49 and femoral head 45 components detailed above, it is intended that these be modular in nature and compatible with one or more total joint systems currently available. Thus, the socket liner 49 described for the purposes of this disclosure will be affixed to a commercially available socket (or acetabular) shell 50 or the liner itself may be directly affixed to bone with polymethylmethacrylate (PMMA) cement depending on the application. In the case of direct PMMA fixation to bone, the back surface of the socket liner 49 component is molded to allow for decreased shear and an increased cement-implant bond. The femoral head component is modular and machined to allow for stable impaction onto a morse or equivalent machine taper on commercially available femoral stem components. The materials used are chosen to decrease the risk of significant galvanic corrosion from mismatched metals.

The devices described in this application are readily adapted to joints other than the hip. As such, TJRs that incorporate electromagnetic induction for use in the knee (including isolated replacement of the patellofemoral joint), and ankle are useful embodiments. Total joint replacements that are applied to the upper limb (shoulder, elbow, and wrist) may also achieve joint angular velocities sufficient for electromagnetic induction to provide reduced friction between bearing surfaces. These upper limb joint replacements are covered under this description as their utility and design are substantially the same as described for the lower limb total joint replacements.

Figure 5:
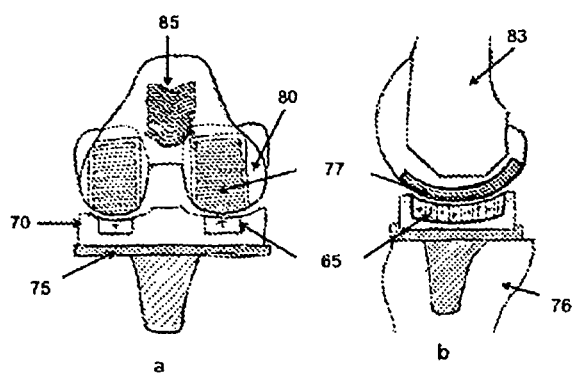
FIG. 5 illustrates the application of electromagnetic induction principles to total knee replacement. The embodiment includes the integration of two or more linear permanent magnet arrays (Halbach shown) embedded within the liner of the tibial component which is configured to be compatible with the locking mechanism inherent to available tibial tray component designs. The frontal view is shown in (a) and the profile view is shown in (b).
Figure 6:
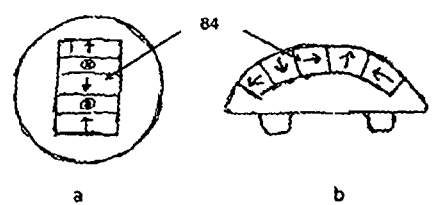
FIG. 6 illustrates the patellar component used for cases where the undersurface of the patella is indicated for replacement. The top view is shown in (a) and the profile view is shown in (b).

In the case of total knee replacement (TKR), the preferred embodiment includes the integration of two or more linear permanent magnet arrays 65 (Halbach or other maximally changing field configuration as described above in principle for THR) embedded within the liner of the tibial component 70 which is configured to be compatible with the locking mechanism inherent to the tibial tray component 75 affixed to the bony tibia 76. FIG. 5 shows the integration of two or more linear permanent magnet arrays (Halbach shown) 65 embedded within the liner 70 of the tibial component which is configured to be compatible with the locking mechanism inherent to current tibial tray 75 component designs. A laminated conducting material configuration 77, slotted and terminated to direct current loops, is embedded within the condyles 80 of the femoral component 80 affixed to the bony femur 83. Induced currents in the conducting material will generate an opposing magnetic field. For cases where the patellofemoral compartment is resurfaced, the central trochlear groove 85 on the femoral component also has a laminated conducting configuration embedded. The frontal view is shown in (a) and the profile view is shown in (b). For cases where the undersurface of the patella is indicated for replacement in addition to the medial and lateral compartments of the knee, a planar or curved permanent magnet array 84 is embedded into the patellar component (FIG. 6). A laminated conducting material configuration (as described previously) is also embedded within the opposing trochlear (central) groove region of the femoral component 85 to allow for the induction of currents and generation of repulsive magnetic fields during joint motion for all three joint compartments. The patellofemoral element of this embodiment would also be applied for cases where replacement of this knee joint compartment alone is indicated.

Figure 7:
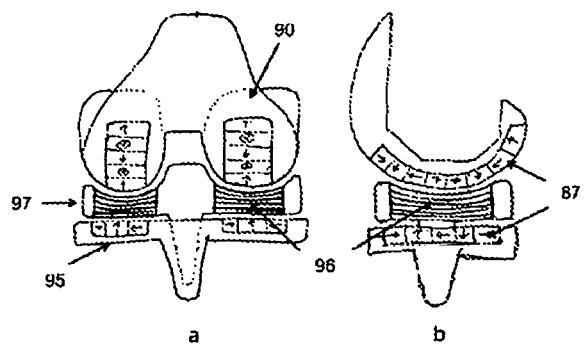
FIG. 7 illustrates the dual bearing embodiment of the TKR whereby permanent magnet arrays (Halbach shown) are embedded within the condyles of the femoral component and within the top surface of the tibial tray component. The frontal view is shown in (a) and the profile view is shown in (b).

Analogous to the dual bearing embodiment of the THR depicted in FIG. 4, the TKR described above may be augmented by embedding permanent magnet arrays 87 within the condyles 90 of the femoral component and within the top surface of the tibial tray 95 component. A laminated conducting material configuration 96 is embedded within the tibial liner 97 and this component articulates as an intercalated segment between these two arrays with currents induced at its top and bottom surfaces. The intercalated tibial liner is constrained to allow for rotation at the tray-liner articulation while flexion-extension knee range of motion occurs at the condyle-liner articulations. Induced currents and stable repulsive magnetic fields generated at these articulations is intended to promote separation of the bearing surfaces involved with a resultant decrease in wear particles. This alternative embodiment is depicted in FIG. 7.

Figure 8:
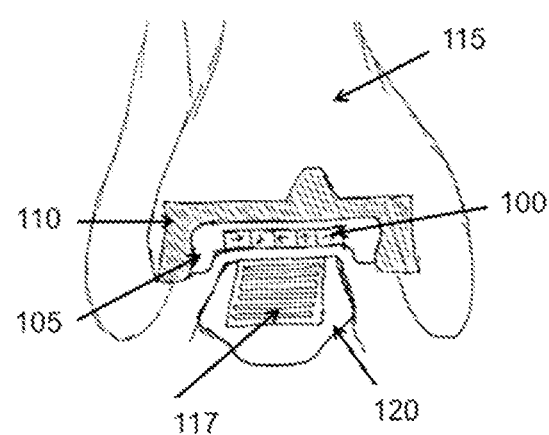
FIG. 8 provides a frontal view of a total ankle replacement (TAR) device. The embodiment includes the integration of a planar or curved permanent magnet array (Halbach shown) embedded within the liner of the distal tibial component.

For the case of total ankle replacement (TAR), the preferred embodiment includes the integration of a planar or curved permanent magnet array (Halbach or other maximally changing field configuration as described in principle above) 100 embedded within the liner 105 of the distal tibial component 110 which is configured to be compatible with the locking mechanism inherent to current tibial component designs or molded to allow for direct cement fixation to the host distal tibial bone 115. A laminated conducting material configuration 117 (as described previously)—in which induced currents will generate an opposing magnetic field—is embedded within the talar component 120 (FIG. 8). As for the dual bearing embodiments described above for both the hip and knee, an alternative embodiment for the TAR includes the integration of an intercalated segment and dual permanent magnet arrays. The arrays are embedded within the distal tibial liner 105 and within the talar component 120, both of which are affixed to bone. A laminated conducting material configuration (as described above) is embedded within an intercalated segment between these two arrays with currents induced at its top and bottom surfaces. The intercalated implant is constrained to allow for rotation at the superior articulation while flexion-extension ankle range of motion occurs at the inferior articulation. Induced currents and stable repulsive magnetic fields generated at these articulations promotes separation of the bearing surfaces involved and will likely result in decreased wear particles.

With respect to the bearing surfaces used in the embodiments for the current invention, biocompatible coatings that exhibit low wear, high strength, increased wettability, and high magnetic permeability, are incorporated to seal the permanent magnet arrays and conducting material from the synovial (joint) fluid. Several coatings are considered which include but are not limited to: titanium nitride, high density polyethylenes, cobalt alloys, and nano-composite materials.

Other embodiments of the invention will be readily apparent. This patent application is only intended to be limited by the appended claims.

The invention claimed is:

1. A joint replacement coupling comprising opposing joint surfaces, wherein one of the surfaces has a magnetic portion therein which comprises an array of permanent magnets, and the other of the surfaces is free from permanent magnets and has a conduction portion therein that comprises an electrically conductive surface, the magnets arranged to produce a magnetic field that contacts the conduction portion, the conduction portion positioned so that at least a portion of the conductive surface contacts the magnetic field so that relative motion between the opposing surfaces induces electric current loops in the conductive surface and the electric current loops produce an electromagnetic repulsive force against the magnetic field, wherein the interaction of the electromagnetic repulsive force against the magnetic field repels the joint surfaces and reduces friction between the joint surfaces during the relative motion.

2. The joint replacement coupling of claim 1 wherein one of the opposing joint surfaces is located on a socket and the other opposing joint surface is located on a head.

3. The joint replacement coupling of claim 2, wherein the socket comprises a liner in which the array of permanent magnets is embedded, wherein the array of permanent magnets comprises a plurality of adjacent permanent magnets arranged in a hemi-spherical Halbach array, and the socket is configured for connection to a shell or a bone.

4. The joint replacement coupling of claim 2, wherein the head comprises a ball containing the array of permanent magnets, wherein the array of permanent magnets comprises a plurality of adjacent permanent magnets arranged in a hemi-spherical Halbach array, and the head is configured for connection either directly to bone or to an implant that is configured for connection to bone.

5. The joint replacement coupling of claim 2, wherein the array of permanent magnets comprises a hemi-spherical Halbach array implanted within the socket, and wherein the head comprises the conductive surface.

6. The joint replacement coupling of claim 5, wherein the Halbach array further comprises:
   interstitial permanent magnets inserted in the Halbach array or
   permanent magnets shaped to focus magnetic flux in an alternating pole pattern.

7. The joint replacement coupling of claim 2, wherein the conduction portion is flat or arc shaped.

8. The joint replacement coupling of claim 2, wherein the head comprises a bifurcated head with two condyles and the socket comprises a bifurcated socket with two condyles.

9. The joint replacement coupling of claim 2, wherein the magnetic field is a changing magnetic field directed outwardly from the magnetic portion.

10. The joint replacement coupling of claim 2, wherein the magnets are rare earth permanent magnets,
   wherein the socket or the head comprises the conductive surface.

11. The joint replacement coupling of claim 2, wherein the conductive surface comprises copper, aluminum, or a composite of a polymer or a ceramic that incorporates carbon nanotubes or graphene.

12. The joint replacement coupling of claim 2, wherein the conductive surface comprises spherically-shaped layers of a conductor that are slotted and terminated at sheet ends to direct currents.

13. The joint replacement coupling of claim 2, wherein most or all of the head surface is the conductive surface.

14. The joint replacement coupling of claim 2, wherein the head comprises the electrically conductive surface covering a spherical core.

15. The joint replacement coupling of claim 2, wherein the conduction portion comprises alternating layers of
   a conductive material layer, and
   an insulating layer, the layers spherically shaped and covering a spherical core;
   wherein the conduction portion comprises thermally conductive metal, wherein the metal comprises heat sinks.

16. The joint replacement coupling of claim 2, wherein the socket fits in a shell or is directly connectable to bone, and
   the head is connectable to an implant that is configured for connection to bone.

17. The joint replacement coupling of claim 2, wherein the relative motion is along a path that is an arc-shaped path or flat path between the socket and head.

18. The joint replacement coupling of claim 2, wherein the joint replacement coupling is a total hip replacement and
   the head comprises a femoral head having a femoral head bearing surface, the femoral head configured for connection to a femoral stem to be fixed in bone; and
   the socket comprises an acetabular socket having a bearing surface that has a round concave portion that receives the femoral head bearing surface, the socket configured for connection to a shell or bone.

19. The joint replacement coupling of claim 2, wherein the opposing joint surfaces are coated with titanium nitride, high density polyethylene, a cobalt alloy, or a composite of a polymer or a ceramic that incorporates carbon nanotubes or graphene.

20. The joint replacement coupling of claim 2, wherein the conducting conduction portion is spherical in shape.

* * * * *